(12) United States Patent
Yao et al.

(10) Patent No.: US 10,537,460 B2
(45) Date of Patent: Jan. 21, 2020

(54) DEVICE AND METHOD FOR ELEVATING A DISTAL EXTREMITY

(71) Applicant: Elevate Braces, LLC, Oakland, CA (US)

(72) Inventors: Jeffrey Yao, Menlo Park, CA (US); Andrew Miller, Oakland, CA (US); Timothy Lew, Oakland, CA (US)

(73) Assignee: ELEVATE BRACES, LLC, Oakland, CA (US)

( * ) Notice: Subject to any disclaimer, the term of this patent is extended or adjusted under 35 U.S.C. 154(b) by 579 days.

(21) Appl. No.: 14/856,201

(22) Filed: Sep. 16, 2015

(65) Prior Publication Data

US 2016/0074205 A1 Mar. 17, 2016

Related U.S. Application Data

(60) Provisional application No. 62/051,814, filed on Sep. 17, 2014.

(51) Int. Cl.
*A61F 5/00* (2006.01)
*A61F 5/37* (2006.01)

(52) U.S. Cl.
CPC ............ *A61F 5/3738* (2013.01); *A61F 5/373* (2013.01)

(58) Field of Classification Search
CPC ...... A61F 5/3738; A61F 5/373; A61F 5/3761; A61F 5/3723

USPC ....... 602/4, 20; 2/44, 45; 128/878, 879, 869, 128/846; D24/190
See application file for complete search history.

(56) References Cited

U.S. PATENT DOCUMENTS

| | | | | |
|---|---|---|---|---|
| 868,298 | A | * | 10/1907 | Siner ............................... 24/702 |
| 1,428,358 | A | * | 9/1922 | Burbery ............. A44B 11/2584 24/702 |
| 3,404,680 | A | * | 10/1968 | Guttman ............... A61F 5/3738 602/4 |
| 4,372,301 | A | * | 2/1983 | Hubbard ............... A61F 5/3738 24/265 R |
| 8,196,588 | B1 | * | 6/2012 | Krenzel ............... A61F 5/3738 602/4 |
| 8,454,544 | B2 | * | 6/2013 | Barnes .................. A61F 5/3738 602/19 |
| 2007/0129657 | A1 | * | 6/2007 | Fisher ................... A61F 5/3738 602/4 |
| 2009/0218464 | A1 | * | 9/2009 | Kato .................... B60R 13/0206 248/316.7 |
| 2010/0152635 | A1 | * | 6/2010 | Borden ................. A61F 5/3738 602/4 |

* cited by examiner

*Primary Examiner* — Kim M Lewis
(74) *Attorney, Agent, or Firm* — Nixon Peabody LLP

(57) ABSTRACT

An apparatus with a limb component configured to be couplable to a body component to immobilize and secure a distal extremity. The body component includes a belt strap and an over-the-shoulder strap. An attachment mechanism configured to couple the limb component to the body component and the attachment point is located above a user's heart when the apparatus is worn by the user.

15 Claims, 14 Drawing Sheets

DEVICE AND METHOD FOR ELEVATING A DISTAL EXTREMITY

CROSS REFERENCE TO RELATED APPLICATIONS

This application claims priority to U.S. Provisional Application No. 62/051,814, entitled Device and Method for Elevating a Distal Extremity, filed Sep. 17, 2014, the contents of which are entirely incorporated by reference herein.

FIELD

The present disclosure relates generally to an apparatus and method to elevate a distal extremity above the level of the heart, and more particularly to an apparatus and method to temporarily restrain a distal extremity such as an arm, wrist, or hand above the heart, with an attachment and release mechanism.

BACKGROUND

Devices have been used to elevate and/or immobilize the distal extremities of the human body above the heart for various purposes, such as reducing swelling and reducing pain after trauma or surgery. These devices can be fabric slings or foam blocks that sufficiently limit the motion of the immobilized limb in a desired location, above the heart. These devices are cumbersome and/or difficult to put on and/or remove.

BRIEF DESCRIPTION OF THE DRAWINGS

Implementations of the present technology will now be described, by way of example only, with reference to the attached figures, wherein.

Figure 1:
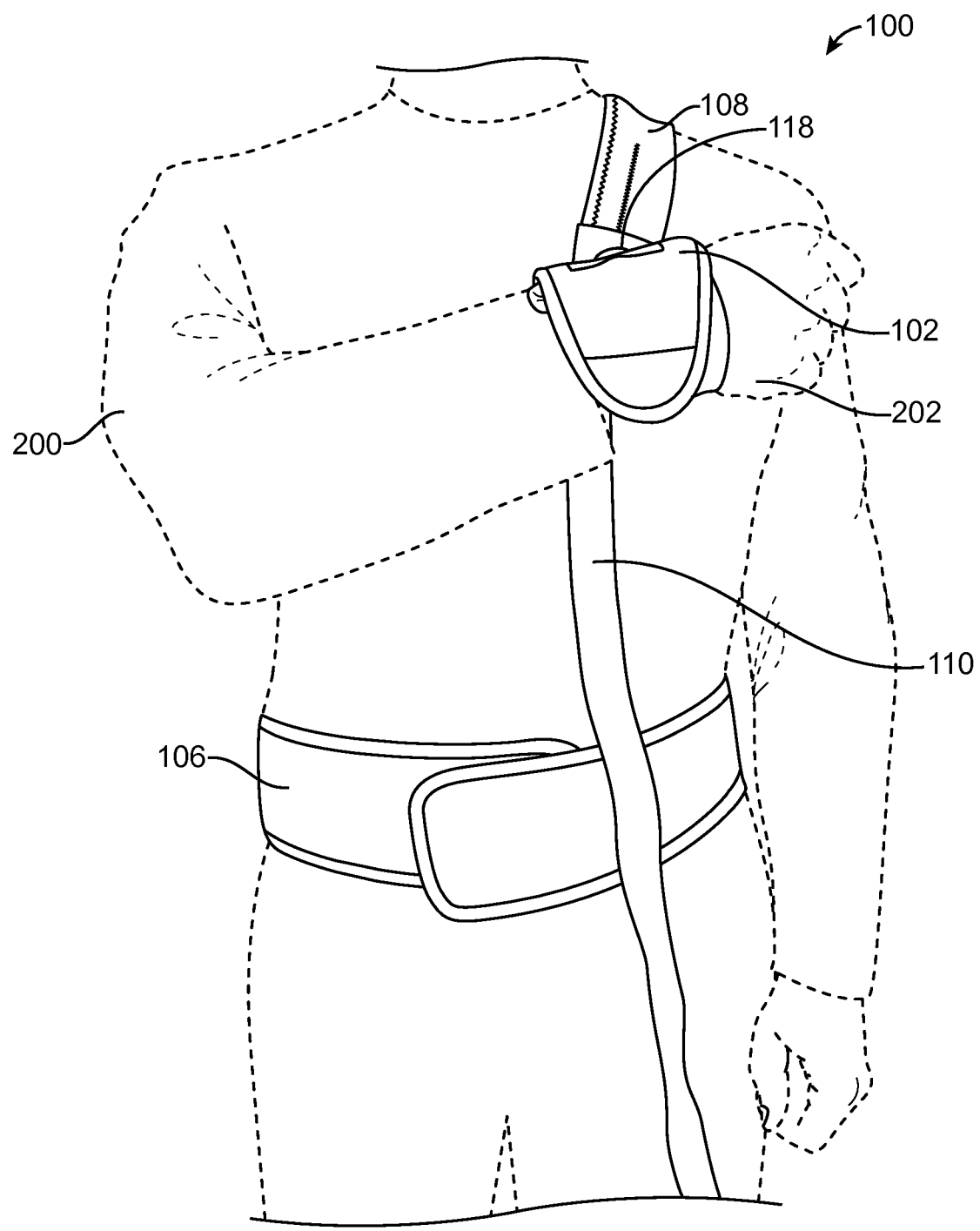
FIG. 1 is a front perspective view of an example embodiment of a brace worn by a patient secured in an elevate position.

It is understood that other configurations of the technology will become readily apparent to those skilled in the art from the following detailed description, wherein various configurations of the subject technology are shown and described by way of illustration. The subject technology is capable of other and different configurations and its several details are capable of modification in various respects without departing from the scope of the subject technology. Accordingly, the detailed description and drawings are to be regarded as illustrative and not restrictive in nature.

DETAILED DESCRIPTION

A reference to an element in the singular is not intended to mean "one and only one" unless specifically stated, but rather "one or more." The term "some" refers to one or more. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The present disclosure related to an apparatus and method to at least temporarily restrain an extremity such as an arm, wrist, or hand above the heart. The apparatus can include a limb component to be secured on or around the extremity and a body component to be secured to a patient. The apparatus can at least temporarily restrain the extremity by coupling the limb component to the body component via an attachment mechanism. The attachment mechanism can be formed by coupling an attachment portion disposed on the limb component and a corresponding attachment portion disposed on the body component. The body component can support the weight of the immobilized limb and distribute the weight throughout the brace of the present disclosure.

The limb component is adjustable, can be used for either left or right sides, and can be sized to fit different hand sizes, wrist sizes, elbow sizes, and forearm sizes. In at least one embodiment, the limb portion is an adjustable wrist component capable of wrapping around a wrist and supporting the weight of an arm.

The body component can have an adjustable belt strap and an over-the-shoulder adjustable strap having the corresponding attachment portion. The limb component can attach to the body component using the attachment portion. The attachment portion can be a magnetic connector and/or a mechanical connector, such as a snap, button, buckle, clasp, pin, or hook and loop fastener or any combination thereof. The limb component is, therefore, adapted to be easily detachable from the body component to allow for movement of the limb. When detached, the limb can be stretched and maintain a range of motion while recovering or healing. In at least one embodiment, a combined magnetic and mechanical connector can be used to facilitate attaching of the distal extremity in an elevated position relative to the heart. Additionally, in various embodiments, the over-the-shoulder strap can have an elastic material for added comfort to a user, as will be discussed in further detail below.

The present disclosure provides for a brace used to elevate an upper distal extremity above the heart, such as a hand, wrist, or forearm. The brace provides support and elevation for all aspects of the distal arm to be raised above the heart to reduce swelling after injury (e.g., acute or chronic) or after surgery (e.g., iatrogenic).

The body component can has have an adjustable belt strap (or torso strap) and at least one over-the-shoulder adjustable strap. The body component is adjustable and can be used to brace right and/or left extremities. In implementations with a belt strap, the weight of the immobilized limb can be transferred from the over-the-shoulder strap to the belt strap.

The limb component can have a male attachment point that mates to a corresponding female attachment point above the heart on the brace that fits around the body. A user, or patient, can install and remove the apparatus by wearing the belt strap at the waist and attaching the limb component to the over-the-shoulder strap. The belt strap can also be a torso strap to be wrapped around a user's torso.

A handle attached to the over-the-shoulder strap can be used to aid in installing and removing of the apparatus. The user can hold the handle with a free hand to stabilize the over-the-shoulder strap so that the limb component can be coupled with the over-the-shoulder strap at a point above the heart. In at least one embodiment, the handle is an elongated strap that extends below the user's waist. In other embodiments, the handle can be a loop in the strap extending below attachment point.

The belt strap and over-the-shoulder strap are adjustable such that users of different sizes can adjust the brace so that the hand is elevated above the heart. The torso strap and over-the-shoulder strap can be adjustable by hook and loop fasteners, sliding fasteners, or other known adjustable fasteners to shorten or lengthen the belt strap and/or the over-the-shoulder strap. The over-the-shoulder strap can have elastic material and/or can be padded for added comfort to the user. The padding can be foam, neoprene, rubber, or any other softening material known in the art.

The over-the-shoulder strap can include a resting component for the hand. The resting component can be a grip, or a demarked area by color or other markings. The resting component can also be used to aid in coupling of the wrist component to the over-the-shoulder strap by showing an ideal location for placing the hand while coupling.

The brace and its components can be made of any material known in the art, including, but not limited to, neoprene, nylon, polymer threads, natural or synthetic rubbers, etc., and combinations thereof.

FIG. 1 illustrates a brace 100 having a strap 102 configured to wrap around a wrist 202 or other portion of the arm to be immobilized. The disclosed embodiments herein show the strap 102 around a wrist, and thus for ease of convenience it shall be referred to as "wrist strap 102" for convenience, although it is to be understood that wrist strap 102 can encompass other portions of the arm and may not encompass the wrist). The wrist strap 102 is removeably coupled to an over-the-shoulder strap 108, such that the user's hand is secured at a point above the user's heart. The wrist strap 102 can be decoupled to allow the arm to move freely.

The wrist strap 102 can be of varying lengths configured to protect and support various portions of the wearers arm, wrist, or hand. In at least one embodiment, the wrist strap can extend up over the hand of the wearer leaving a thumb portion open above the carpometacarpal joint. In other embodiments, the wrist strap can extend below the elbow of the wearer leaving the elbow exposed above impingements of the Median, Ulnar, or Radial nerves. 11. In yet other embodiments, the wrist strap can extend up the hand and thumb above the interphalangeal joint.

The over-the-shoulder strap 108 also has a handle 110 that extends from over-the-shoulder-strap 108 to just below a torso strap 106 that encircles the torso (about the waist in FIG. 1). The handle 110 allows a user's non-immobilized hand to pull the over-the-shoulder strap 108 taught when coupling or decoupling the wrist strap 102. Handle 110 is couplable to the torso strap 106 by hook and loop fasteners, a male/female clip, magnets, hook and loop fasteners (such as Velcro) or other quick release; the present disclosure is not limited to the form of attachment. In other embodiments, the handle 110 can be a loop extending from the over-the-shoulder strap 108, but terminating above the belt strap 106.

In at least one embodiment, the torso strap 106, over-the-shoulder strap 108, and handle 110 are designed to be cut to the desired length for each individual patient. Each is provided with sufficient length for most users, and can be trimmed to the appropriate length Each can also be secured to itself using hook and loop fasteners, such as Velcro.

The torso strap 106 can be of sufficient width to provide support for the elevated wrist strap 102 and sufficient length to wrap entirely around a patient's torso and be secured. The torso strap 106 is wider than the over-the-shoulder strap 108 for increased comfort while wearing and elevating the wrist strap 102. The torso strap 106 can include padding to increase comfort and be made of neoprene, polymer threads, synthetic rubbers, etc. or combinations thereof.

As discussed in more detail below, the wrist strap 102 is adapted to be released from the over-the-shoulder strap 108 by moving the immobilized wrist 202 in upwards direction. In other embodiments, the wrist component is adapted to be released from the over-the-shoulder strap 108 by moving the immobilized extremity 202 in a left or right direction. The wrist strap 102 can also be adapted to be released by activating a release mechanism, such as a draw cord or depressing a release catch with the user's free, non-immobilized hand.

FIG. 1 further illustrates the use of the wrist strap 102 of the brace 100 for a wrist to secure a hand above the heart, although it is to be understood that the brace 100 can be implemented to secure a wrist, forearm, elbow, and/or any other distal extremity as well at any point along the torso.

The brace can elevate and restrain various limb components depending on where the limb component is attached on the user's arm. For ease of discussion the described examples herein are directed to wrist support, although the present disclosure is not so limited.

Figure 2:
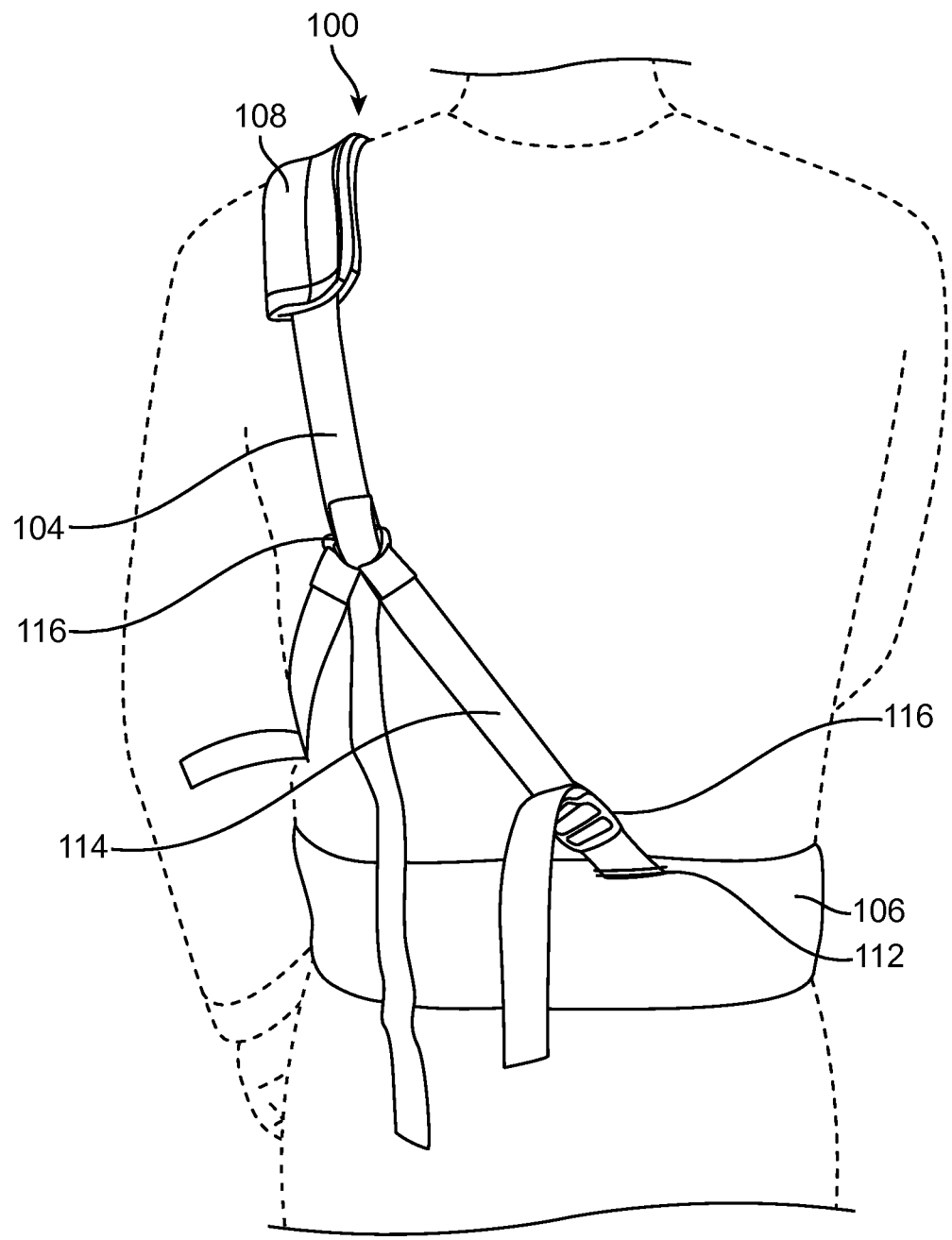
FIG. 2 is a rear perspective view of an example embodiment of a brace worn by a patient.

FIG. 2 is a rear view of a brace 100 and over-the-shoulder strap 108. The torso strap 106 is disposed around the user's hip, waist, or torso. The over-the-shoulder strap 108 of the brace 100 extends upward from the wrist strap 102 in FIG. 1, and wraps over the shoulder opposite from the immobilized limb down a back portion 104. Back portion 104 can extend all the way to torso belt 106 and attach in the manner as noted above for the front. However, additional support can be provided by dispersing the load across torso belt 106.

For such distribution, an adjustable connector 116 joins the end of back portion 104 to several base straps 114 (two are shown, although the present disclosure is not limited to any number), while the opposing ends of straps 114 connect to the torso strap 106 at one or more attachment points 112. Adjustment of connector 116 allows the over-the-shoulder strap 108 and the plurality of base straps 114 to be shortened or lengthened to properly position the brace 100. The one or more adjustment points 116 can be a ladder style slider adjustment, looped D-rings, a slide adjuster, or any combination thereof, although the present disclosure is not limited to any particular type of connector. The ladder style slider can receive the over-the-shoulder strap 108 therethrough and apply a frictional force to prevent unwanted movement of the strap. In at least one embodiment, the over-the-shoulder strap 108 is adjustable and the plurality of base straps 114 are a fixed length. In other embodiments, the over-the-shoulder strap 108 and the plurality of base straps 114 are independently adjustable of the other.

In at least one embodiment, the adjustable connector 116 is a D-ring, triangular shaped ring, or any other polygonal shaped ring to allow adjustment of the over-the-shoulder strap 108 and the plurality of base straps 114. The over-the-shoulder strap 108 passes through the adjustable connector 116 and folds back upon itself and secures to itself by hook and loop fastener. Similarly, each of the plurality of base straps 114 pass through the adjustable connector, and fold back upon themselves, securing by hook and loop fasteners.

As can be appreciated in FIG. 2, the rear portion of the brace 100 has two attachment points 112 each having a base strap 114 extending therefrom, thereby coupling the over-the-shoulder strap 108 with the torso strap 106. The over-shoulder-strap 108 and base straps 114 can utilize one or more times of adjustment connectors 116. For example in FIG. 2, each base strap 114 has ladder style slider an adjustment point 116 and the over-the-shoulder strap 108 has a looped D-ring adjustment point 116.

In at least one embodiment, the brace 100 is disposed around the user's hips or waist with one or more attachment points 112 (for example, one, two, or three attachment points) on the dorsal/posterior portion of the brace 100. The over-the-shoulder strap 108 can attach to the torso strap 106 at the one or more attachment points 112. In some implementations, the one or more attachment points 112 can comprise hook and loop fasteners, clasps, buttons, snaps, hooks, etc. for easy attachment and detachment.

Figure 3:
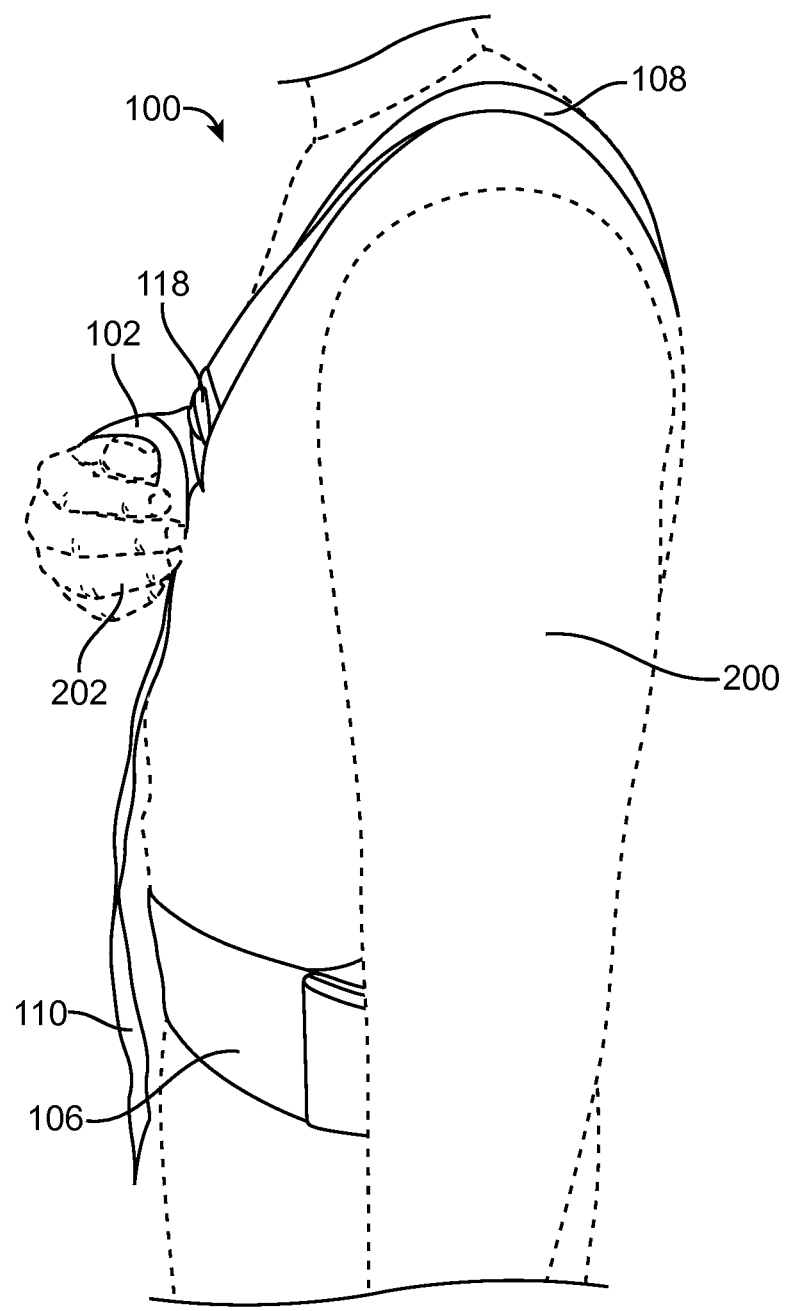
FIG. 3 is a left perspective view of an example embodiment of a brace worn by a patient secured in an elevated position.

FIG. 3 illustrates a left side view of the brace 100 having the wrist strap 102 secured to the body component in an elevate position. The brace 100 preferably positions the immobilized wrist 202 above the heart, and the over-the-shoulder strap 108 extends upwards from the posterior portion of the brace 100 and wraps over the opposite shoulder from the affected limb 202 to provide an attachment point 118. The weight of the immobilized limb 202 is supported by the over-the-shoulder strap 108 as secured to the belt strap 106. The elevation of the immobilized limb 202 can be adjusted by shortening or lengthening the over-the-shoulder strap 108 via the various adjustment options discussed above. The elevation is raised by shortening the over-the-shoulder strap 108, and lowered by lengthening the over-the-shoulder strap 108. The necessary elevation of the immobilized limb 202 can vary between patients based on size and also by necessary treatment plans from surgery or chronic/acute injuries.

As can be appreciated in FIG. 3, the over-the-shoulder strap 108 extends over the opposing shoulder from the immobilized limb. Thus in FIG. 3 the user 200 has a right limb immobilized above the heart, and the over-the-shoulder strap 108 extends over the left shoulder.

Figure 4:
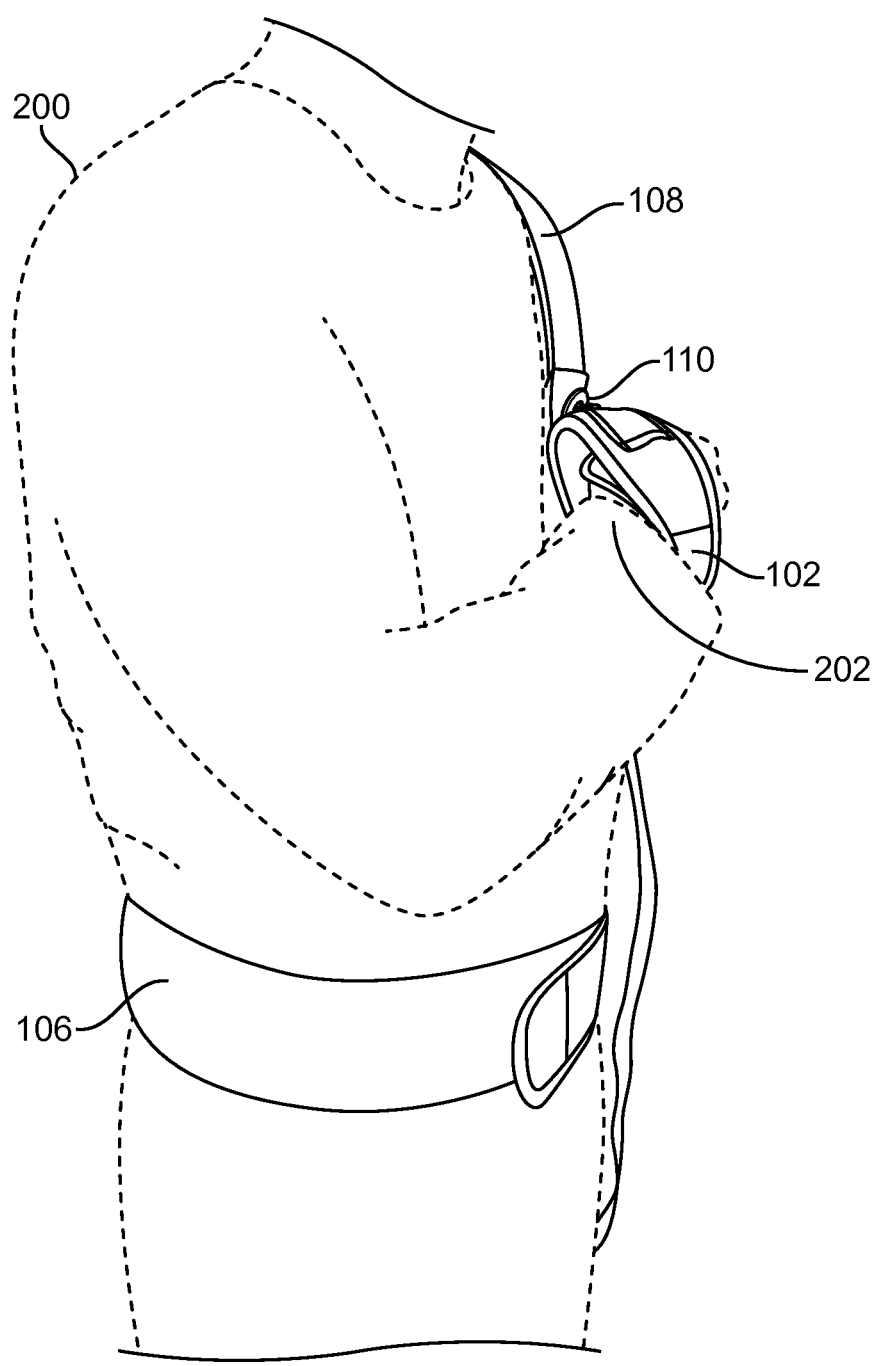
FIG. 4 is a right perspective view of an example embodiment of a brace worn by a patient secured in an elevated position.

FIG. 4 illustrates a right side views of a brace 100 having the wrist strap 102 secured in an elevated position. As can be appreciated in FIG. 4, the torso strap 106 wraps around the user's waist and the immobilized limb 202 is secured in a position above the heart.

Figure 5:
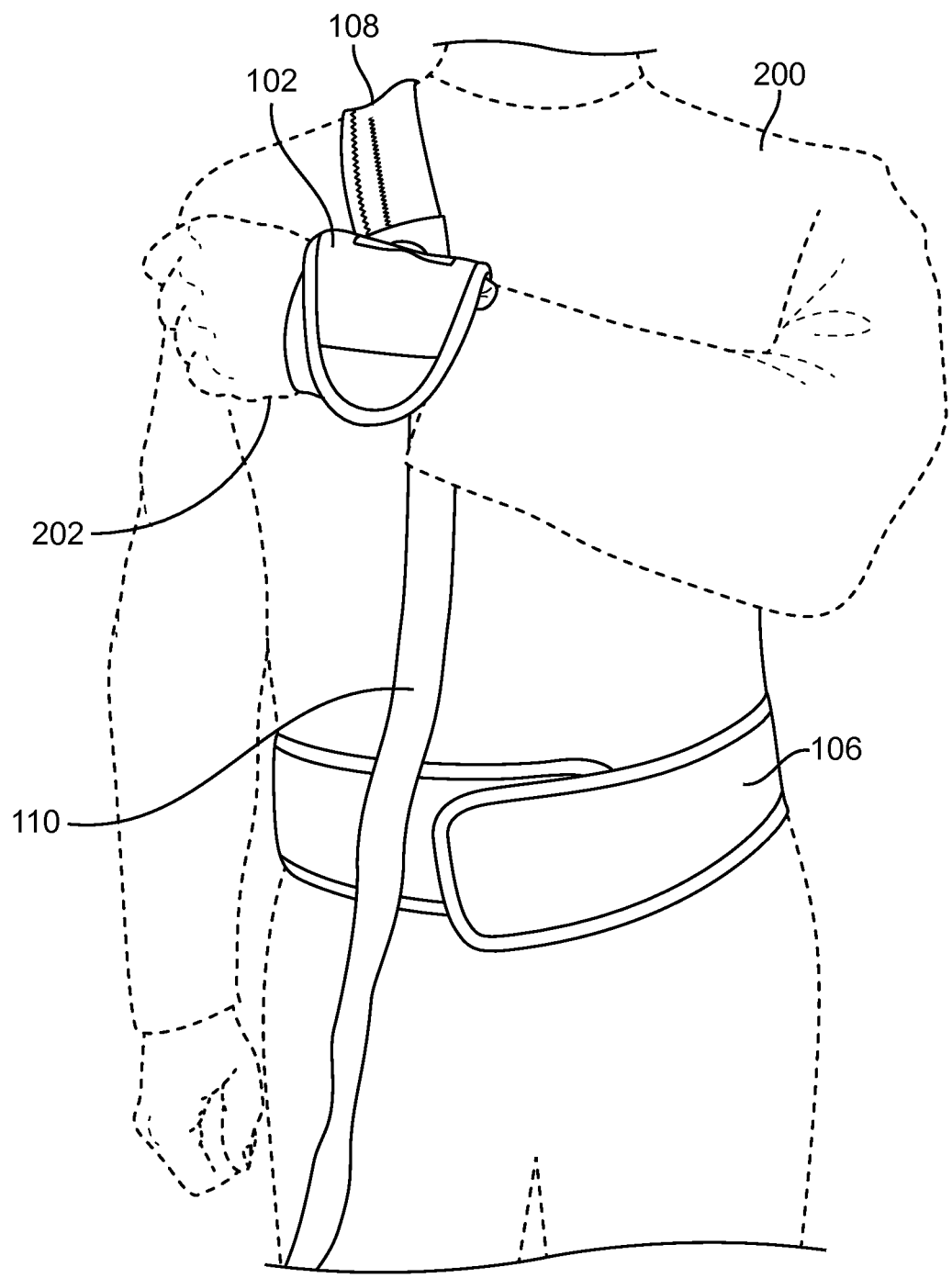
FIG. 5 is a front perspective view of an example embodiment of a brace worn by a patient secured in an alternative elevated position.

FIG. 5 of illustrates a brace 100 coupled in an alternative elevated position. The arrangement is the same as in FIGS. 1-4, save that the left arm is immobilized rather than the right.

Figure 6:
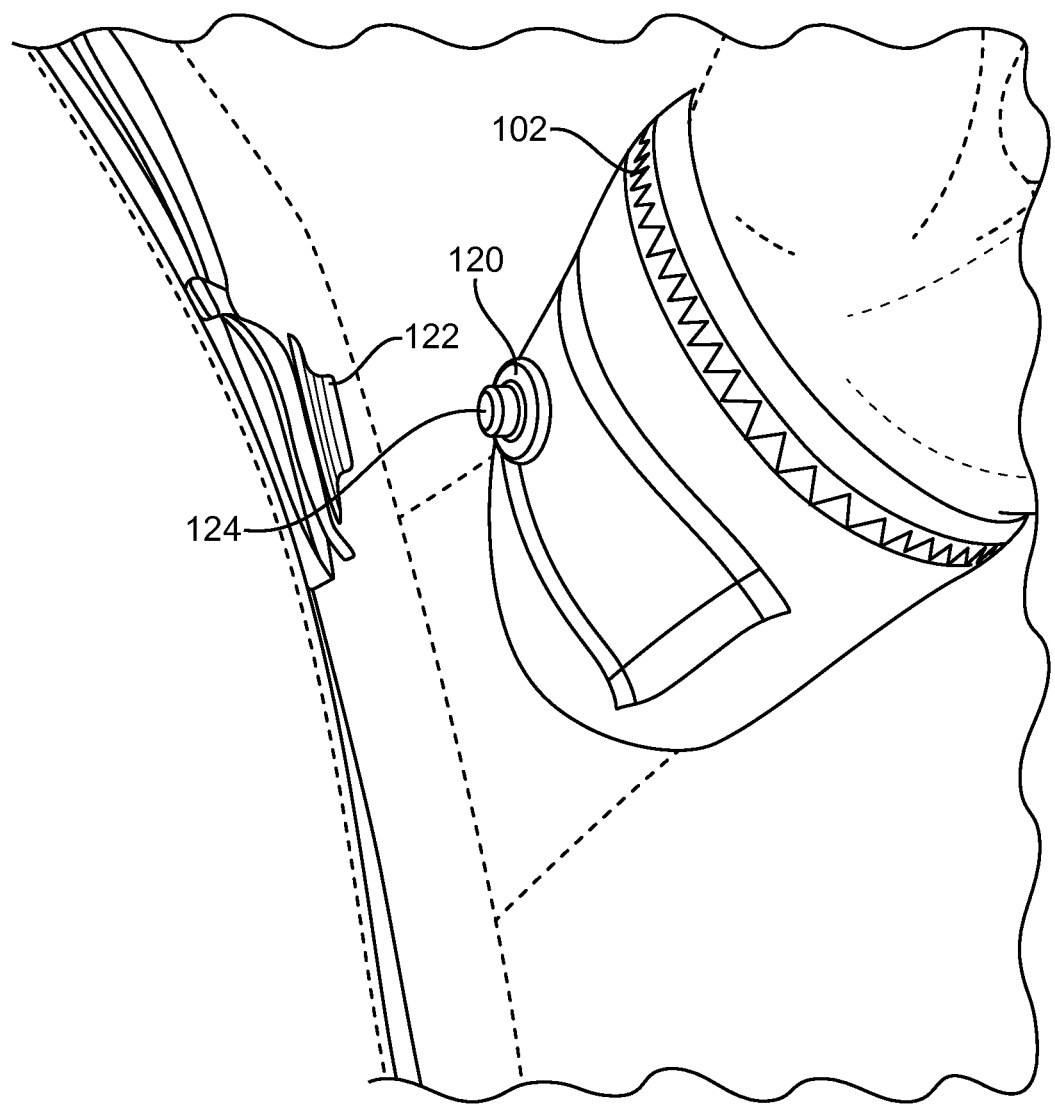
FIG. 6 is a partial perspective view of an example embodiment of a brace worn by a patient and an attachment mechanism in elevated unsecured position.

FIG. 6 illustrates the wrist strap 102 detached from brace 100. The wrist strap 102 is releasably coupled to the over-the-shoulder strap 108 using an first connector 120 on the wrist strap 102 and a corresponding second connector 122 on the over the shoulder strap 108.

Figure 7:
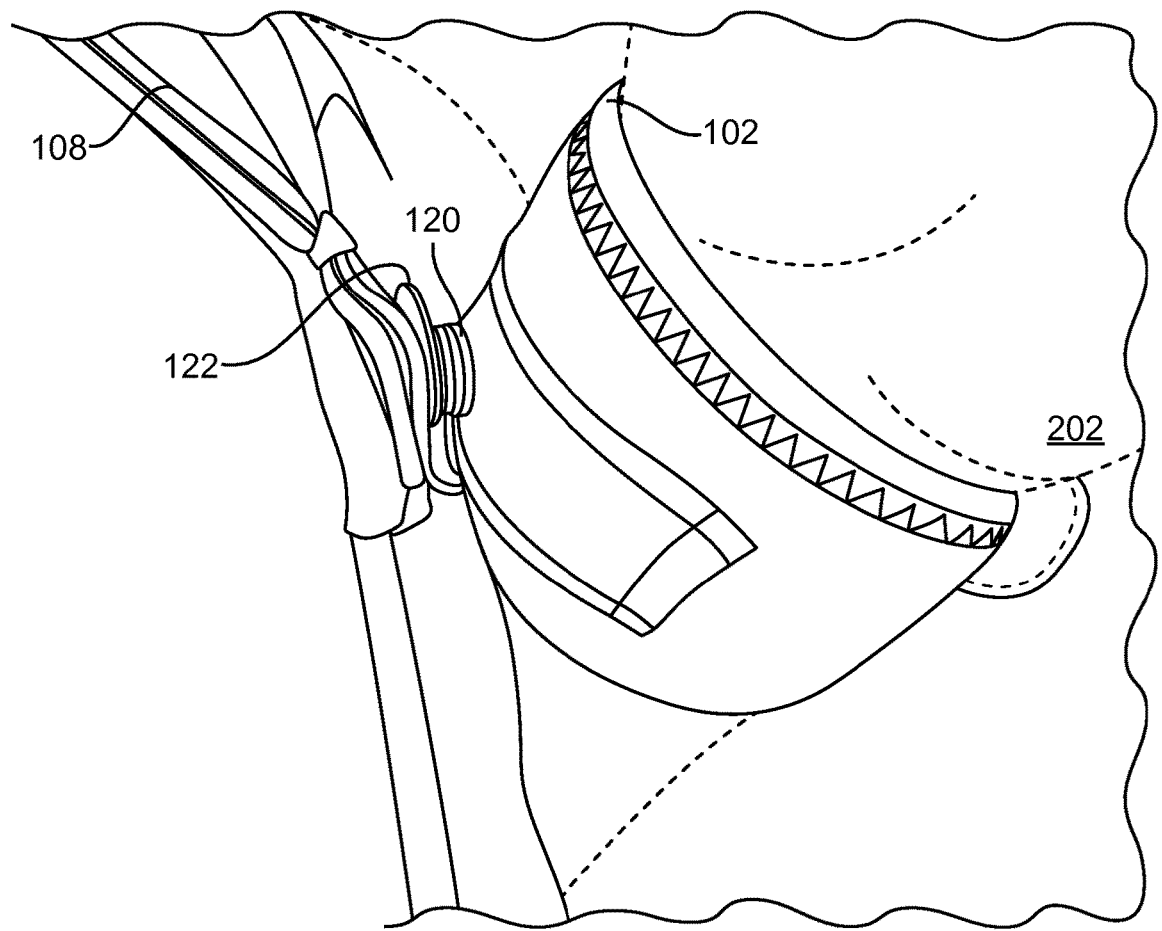
FIG. 7 is a partial perspective view of an example embodiment of a brace worn by a patient and an attachment mechanism in elevated secured position.
Figure 8:
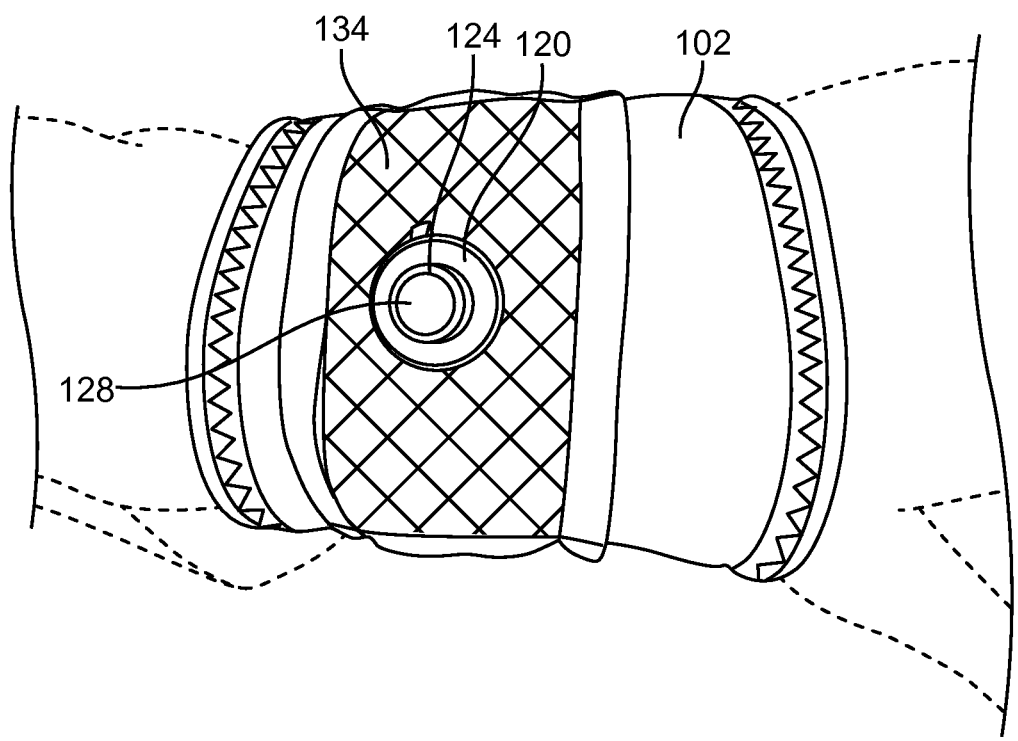
FIG. 8 is a perspective view of an example embodiment of a limb component of a brace having an attachment portion of an attachment mechanism.
Figure 9:
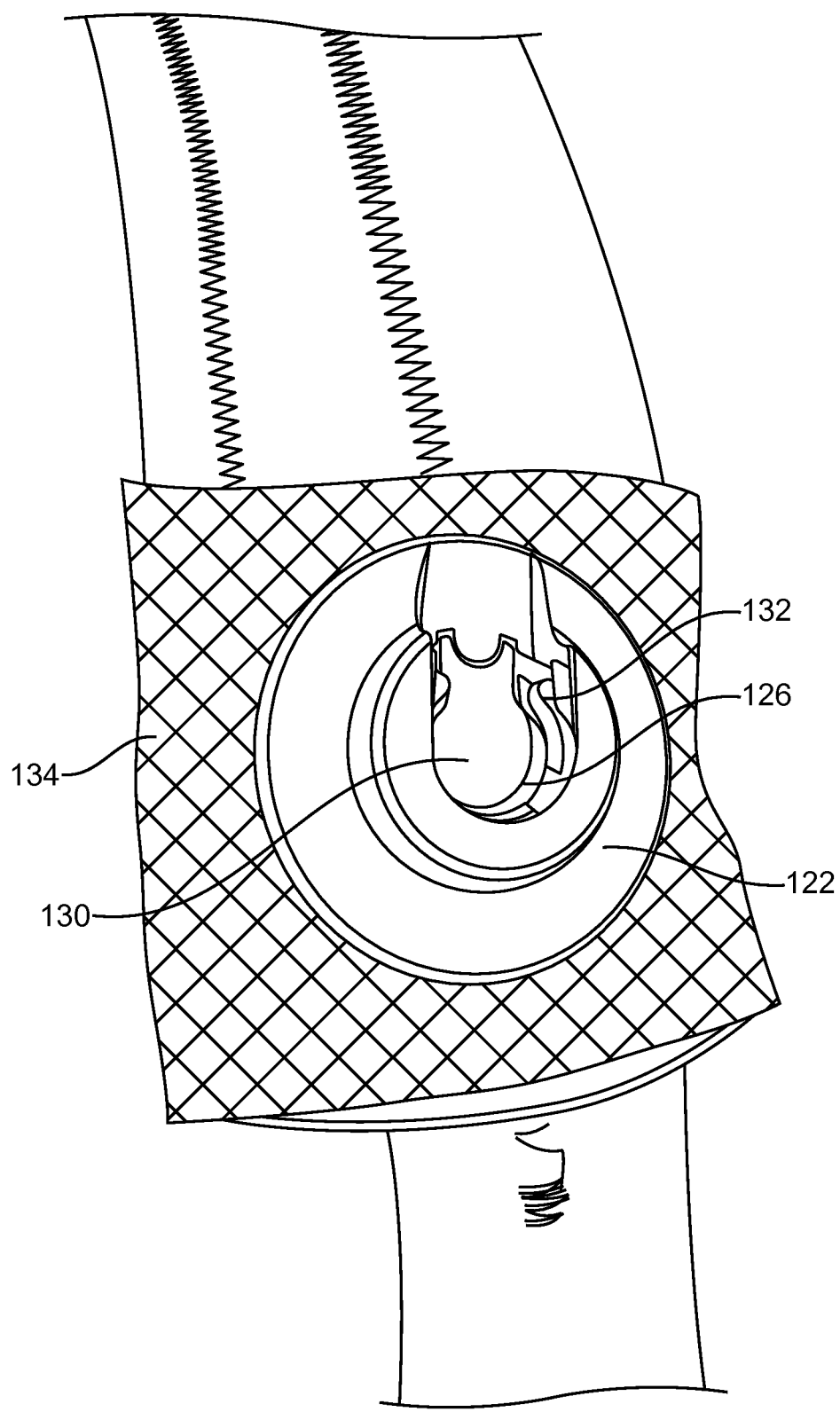
FIG. 9 is a perspective view of an example embodiment of a body component of a brace having a corresponding attachment portion of an attachment mechanism.

Referring now to FIGS. 7-9, the first connector 120 includes a protrusion 124 and the corresponding second connector 122 includes a corresponding groove 126. The protrusion 124 is configured to be received within the groove 126.

In at least one embodiment, the wrist strap 102 is coupled to the over-the-shoulder strap 108 by a magnetic or mechanical connector located on the wrist strap 102 to a corresponding magnetic or mechanical connector located on the over-the-shoulder strap 108. The mechanical connector can be a snap, button, buckle, clasp, pin, or hook and loop fastener or any combination thereof. Attachment can utilize a magnetic mechanism, a mechanical mechanism, or a combination thereof. In at least one embodiment, the attachment mechanism includes a magnetic mechanism and a mechanical mechanism. The magnetic mechanism can attract and index the first connector 120 and the corresponding second connector 122. The mechanical mechanism can provide stability to the wrist strap 102 and allow the weight of the distal extremity to be transferred to the over-the-shoulder strap 108 and remaining portion of the brace 100. The mechanical mechanism can also produce a snap sound to provide an auditory cue to the user that the wrist strap 102 has been secured to the body component 104.

FIG. 7 illustrates a brace 100 having a wrist strap 102 secured in an elevated position to the over-the-shoulder strap 108. The attachment of the first connector 120 with the corresponding second connector 122 securely couples the wrist strap 102 to the over-the-shoulder strap 108, thereby restraining the wrist above the heart. As can be appreciated in FIG. 7, the protrusion 124 is received within the corresponding groove 126 to couple the wrist strap 102.

FIG. 8 illustrates a wrist strap 102 of a brace 100 including the first connector 120. The wrist strap 102 is disposed around the distal extremity 202 of a user 200. The first connector 120 includes the protrusion 124. The protrusion 124 can be a raised bump and have a magnet 128 disposed therein. In at least one embodiment, the wrist strap 102 includes the protrusion 124 and the over-the-shoulder strap 108 includes the groove 126 (shown in FIG. 9). The first connector 120 for the wrist strap 102 can have a magnetic protrusion 124 that interfaces and engages with the groove 126 on the over-the-shoulder strap 108 on the front portion of the user's body. In other embodiments, the attachment portion 120 of the wrist strap 102 can include a groove, or other female attachment mechanism, that interfaces and engages with a protrusion, or other male mechanism, magnetic attachment on the over-the-shoulder strap 108 on the front portion of the user's body.

FIG. 9 illustrates a close-up view of the groove 126 on the wrist strap 102. The groove 126 includes guiding features and mechanical attachment for the protrusion 124. The groove 126 can also include a magnet 130 that when coupled with magnet 128, can support at least a part of the weight of the user's arm. The magnets 128, 130 can generate a magnetic attraction sufficient to prevent a user for pulling them apart, but allowing a user to slide the magnetic surfaces away from one another to separate (See FIG. 13).

To form the connection when magnets are used, the wearer brings protrusion 124 into proximity of groove 126. When close enough, magnetic force will draw protrusion 124 into the groove, either directly into dead center or slight above in the opening of the groove the wearer can either accept or slide down for a dead center fit.

As is known in the magnetics art, it can more difficult to pull magnets directly apart than to slide them relative to each other, and the embodiments of the present disclosure leverage this as the engagement disengagement mechanism. Once coupled, the magnetic attraction will tend to keep wrist strap 102 connected to shoulder strap 108 (due to the difficulty to pull magnetics directly apart). The various straps will all have some degree of slack, such the small movement of the arm away from the body will simply move the straps about without disconnecting the components. Movements of the arm in any other downward or lateral direction about the second connector 122 will not break the magnetic connection because the side walls of the groove 126 prevents the magnets 128, 130 from sliding.

As noted above, since the groove 126 is open at the top the user can disconnect the wrist strap 102 by moving the wrist strap upwards, thereby sliding the magnetic components out of contact with each other; to the extent desirable or necessary, the wearer can use the handle 110 to stabilize shoulder strap to eliminate slack that might otherwise complicate the removal. In other embodiments, the groove 126 can be orientated in any direction to allow the magnets to be slid apart at any angle, such as left or right, or anything therebetween.

As can be appreciated in FIG. 9, the magnet 130 forms a substantially flat back surface of the groove 126. The magnet 130 can be any material capable of inducing a magnetic charge between a similar magnetic element.

The groove 126 also includes a mechanical fastener 132 to securely couple the wrist strap 102 with the body component 104. The mechanical fastener 132 preferably generates an auditory sound indicating to the user properly coupling between the wrist strap 102 and the over-the-shoulder strap 108. The mechanical fastener 132, such as a inwardly facing spring prongs, can provide an audible sound to confirm that the protrusion 124 properly mates with the groove 126, and well as provide minor resistance against removal to prevent unintentional disengagement. The mechanical fastener 132 is decoupable by a user applying an upward force to separate the magnets 128, 130.

In at least one embodiment, the wrist strap 102 and the over-the-shoulder strap 108 have visual indicators 134 for aiding in coupling the wrist strap 102 to the over-the-shoulder strap 108. The visual indicators 134 can be located on either, or both, of the over-the-shoulder strap 108 or wrist strap 102 and can comprise arrows, color indicators, symbols, the shape of a hand, etc., and combinations thereof (shown in FIGS. 9 and 13). In other embodiments, sloping indexing features (e.g., ramp or convex/concave guiding) can also be used for aid in positioning and coupling the wrist component to the over-the-shoulder strap 108. These features aid in intuitive coupling of the wrist component to the over-the-shoulder strap such that the user does not have to see the coupling taking place, but rather can do it intuitively by feel.

Figure 10:
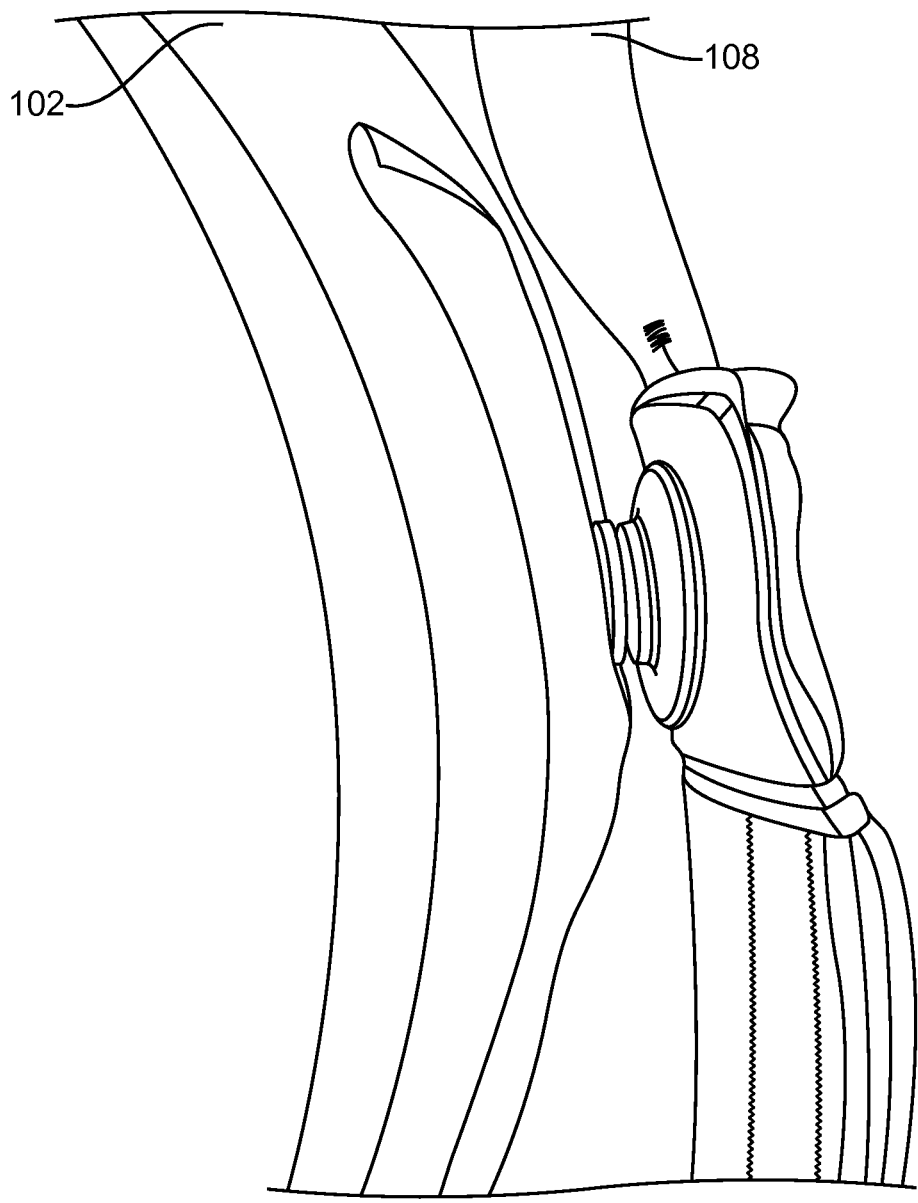
FIG. 10 is a side perspective view of an example embodiment of a brace having a limb component secured to a body component by an attachment mechanism.

FIG. 10 illustrates a close-up view of the wrist strap 102 coupled to the over-the-shoulder strap 108. The protrusion 124 of the wrist strap 102 is received within the groove 126 on the over-the-shoulder strap 108. The protrusion 124 being received within the groove 126 couples the wrist strap 102 with the over-the-shoulder strap 108.

Figure 11:
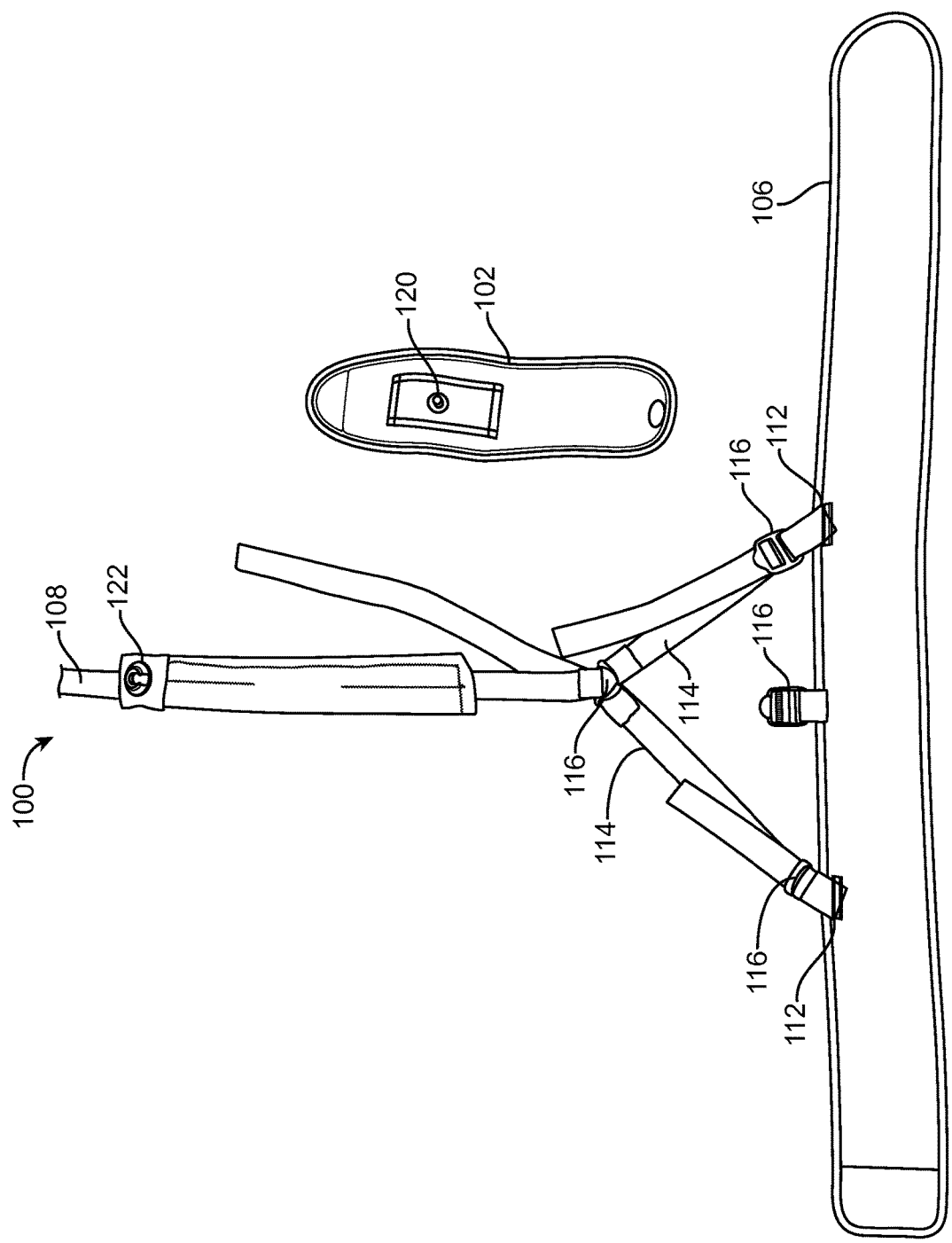
FIG. 11 is a planar view of an example embodiment of an unworn brace having a limb component unsecured from a body component.

FIG. 11 illustrates the brace 100 in an unworn position. The wrist strap 102 is decoupled from the over-the-shoulder strap 108. As can be appreciated in FIG. 11, the brace 100 includes the plurality of base straps 114 and the one or more adjustment points 116.

Figure 12:
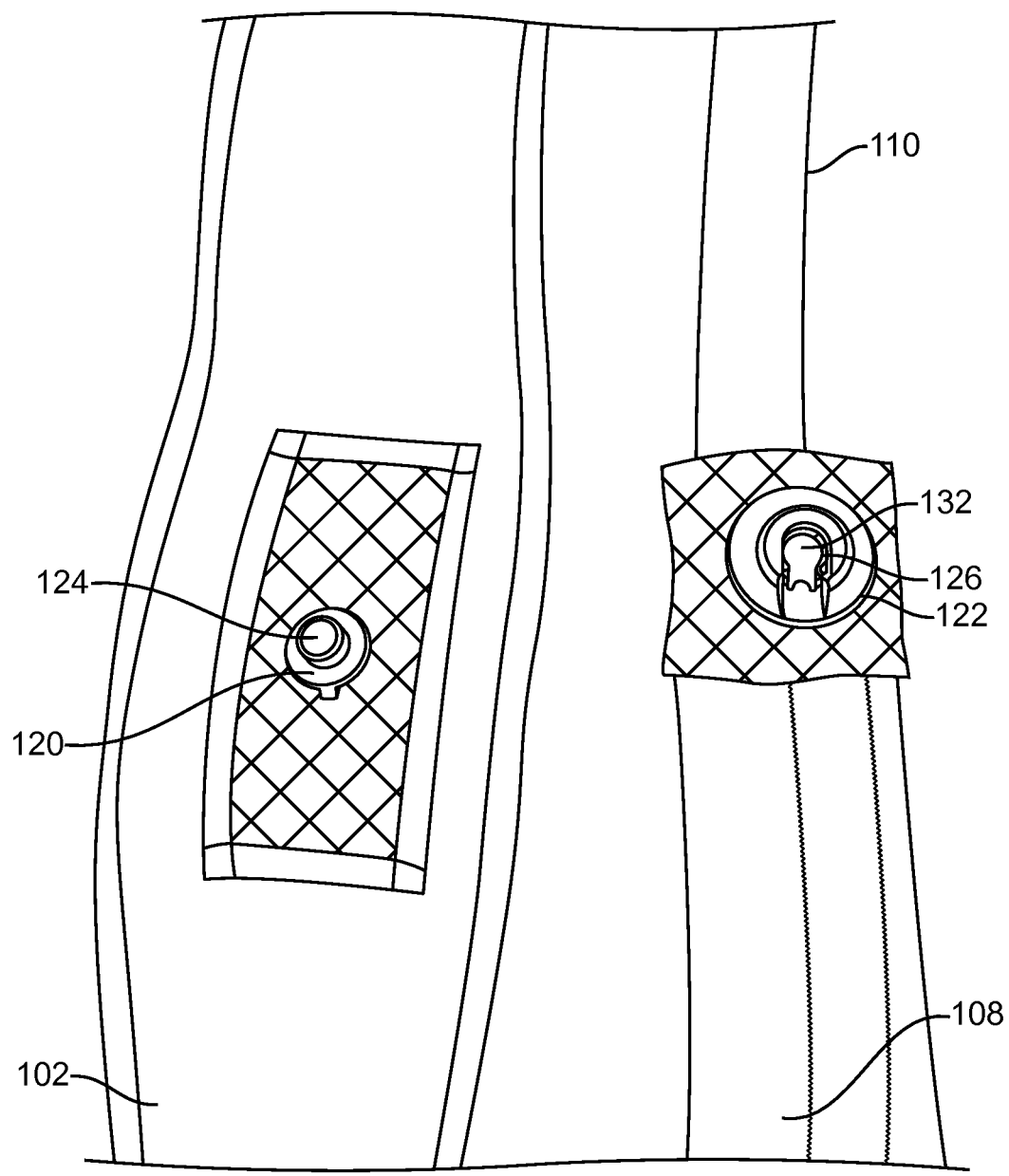
FIG. 12 is an enlarged planar view of an example embodiment of an unworn brace having a limp component with an attachment portion unsecured from a body component with a corresponding attachment portion.

FIG. 12 illustrates the protrusion 124 and groove 126 connectors decoupled one from the other. The protrusion 124 is sized appropriately to be securely received within the groove 126 while also allowing easy coupling and decoupling of the wrist strap 102 from the body component 104.

Figure 13:
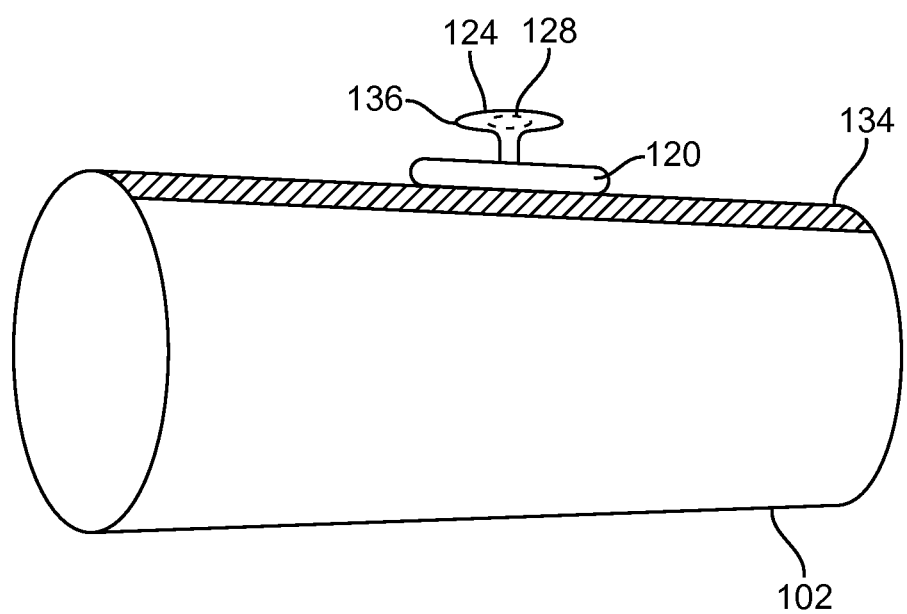
FIG. 13 is a side view of another example embodiment of an unworn limb component.

FIG. 13 illustrates a side view of another example embodiment of the wrist strap 102. The wrist strap 102 has a first connector 120 with protrusion 124. The protrusion 124 includes a ridge 136 to engage with the mechanical fastener 132 of the groove (shown in FIG. 9). The interaction and engagement between the ridge 136 and the mechanical fastener 132 can generate an auditory queue to a user indicating proper engagement between the first connector 120 and the second connector 122. The wrist strap 102 can include a magnet 128 disposed within the first connector 120. The magnet 128 can be a permanent magnet disposed within the protrusion 124 capable of engaging a similarly magnet 132 disposed within the second connector 122. In at least one embodiment, the magnet 132 is a substantially cylindrical disc of magnetically charged iron.

Figure 14:
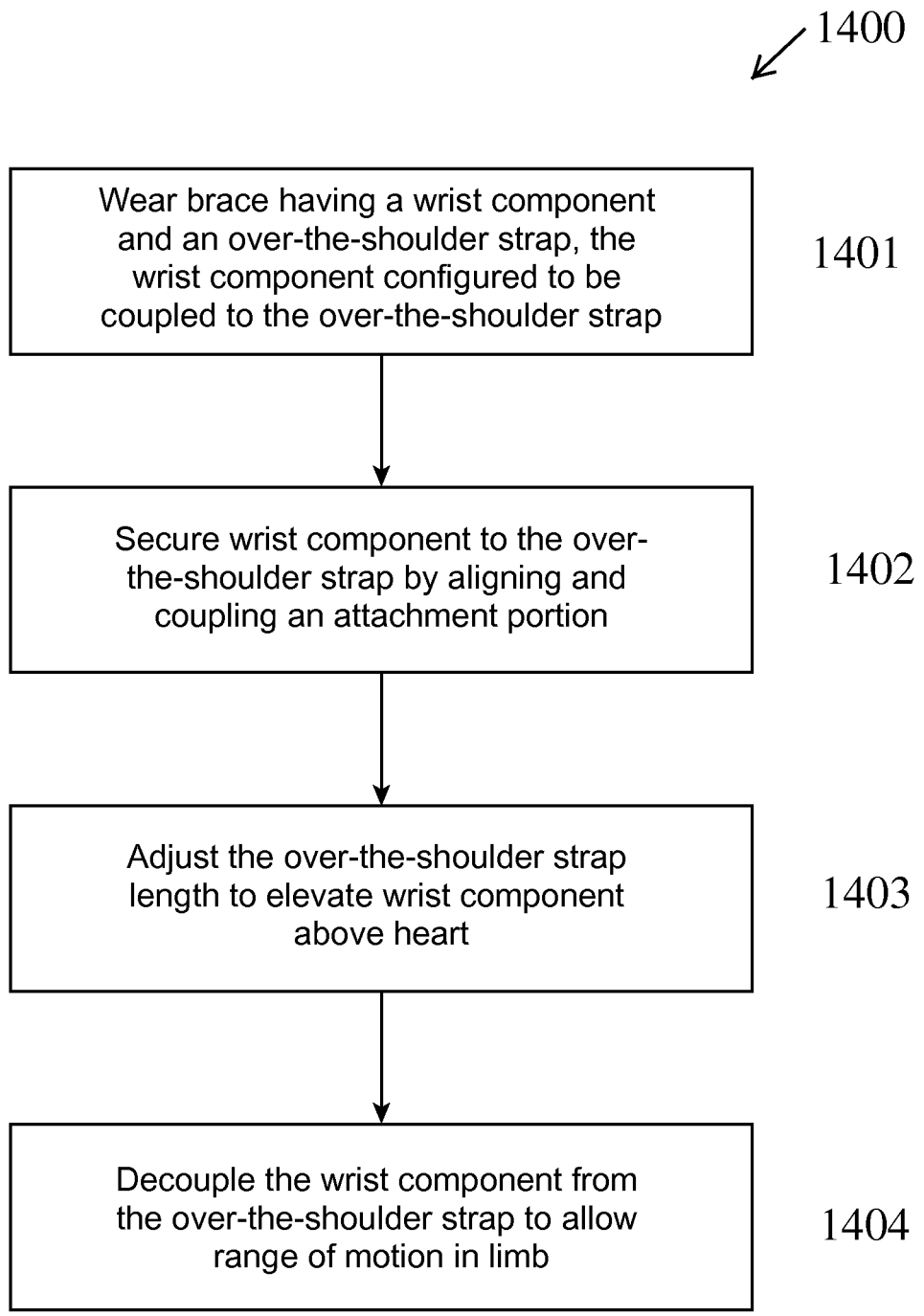
FIG. 14 is a flowchart of an example embodiment of a method for using a elevate brace.

Referring to FIG. 14, a flowchart is presented in accordance with an example embodiment. The example method 1400 is provided by way of example, as there are a variety of ways to carry out the method. The method 1400 described below can be carried out using the configurations illustrated in FIGS. 1-13, for example, and various elements of these figures are referenced in explaining example method 1400. Each block shown in FIG. 14 represents one or more processes, methods or subroutines, carried out in the example method 1400. Furthermore, the illustrated order of blocks is illustrative only and the order of the blocks can change according to the present disclosure. Additional blocks may be added or fewer blocks may be utilized, without departing from this disclosure. The example method 1400 can begin at block 1400.

At block 1401, a brace 100 is worn by a user. The brace has a wrist strap 102, a torso strap 106, and an over-the-shoulder strap 108. The wrist strap 102 is disposed around a distal extremity and has a first connector 120. The torso strap 106 is disposed around a waist, and the over-theshoulder strap 108 disposed over a shoulder opposite the distal extremity. The over-the-shoulder strap 108 includes a second connector 122.

At block 1402, the wrist strap 102 is secured to the over-the-shoulder strap 108 by aligning and coupling the first connector 120 with the second connector 122 in a coupling direction.

At block 1403, the over-the-shoulder strap 108 is adjusted to properly fit the user and elevate the limb component above a heart.

At block 1404, the first connector 120 is decoupled from the second connector 122 by applying a force in a direction opposite the coupling direction.

Although the illustrated embodiments illustrate the brace being used with one hand, other implementations can be realized. For example, the brace can be modified so that it can be used to secure two hands above the heart. This can be accomplished by attaching a second over-the-shoulder strap to the belt strap to extend superior from the posterior of the brace and wrap over the opposite shoulder from a second affected extremity.

The various features of the brace can also be differently configured, depending on the intended use, without departing from the subject technology. By way of example, the adjustment points can be located anywhere on the brace, including the anterior portion, or on the over-the-shoulder strap. As such, various adjustments points can be utilized.

The description of the subject technology is provided to enable any person skilled in the art to practice the various embodiments described herein. While the subject technology has been particularly described with reference to the various figures and embodiments, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these embodiments will be readily apparent to those skilled in the art, and generic principles defined herein may be applied to other embodiments. Thus, many changes and modifications may be made to the subject technology, by one having ordinary skill in the art, without departing from the scope of the subject technology.

What is claimed is:

1. A limb support device for a limb of a wearer, comprising:
    a wrist strap configured to support a portion of an arm of the wearer;
    a first connector on the wrist strap, wherein the first connector is a protrusion comprising a first magnet;
    an over the shoulder strap configured to be worn over a shoulder of the wearer;
    a second connector on the shoulder strap, wherein the second connector is a groove comprising a second magnet, the protrusion receivable within the groove to couple the wrist strap with the over the shoulder strap, wherein the groove is open at a top portion such that the wrist strap is disconnected from the over the shoulder strap by moving the wrist strap upwards to slide the first magnet apart from the second magnet, and wherein the groove is closed on a bottom portion and side portions to secure a magnetic connection between the first magnet and the second magnet;
    a torso belt coupled to both ends of the over the shoulder strap, the torso belt configured to be worn around a torso of the wearer;
    wherein when the wrist strap, the shoulder strap and the torso belt are mounted on the wearer, moving the first connector into engagement with the second connecter magnetically couples the first and second connectors to hold the wrist strap in place and transfer the weight of the arm to the wearer's body, and raising the first connector out of engagement with the second connecter decouples the first and second connectors and allows free movement of the arm.

2. The apparatus of claim 1, wherein first connector includes magnetic attachment portion capable of inducing a magnetic attraction with a magnetic attachment portion of the second connector.

3. The apparatus of claim 1, wherein the over the shoulder strap has an auditory generator upon coupling of the wrist strap with the over the shoulder strap.

4. The apparatus of claim 1, wherein the over the shoulder strap includes a plurality of base straps coupled to the rear of the torso strap.

5. The apparatus of claim 4, wherein the plurality of base straps slidingly couple with the over the shoulder strap at an adjustment point.

6. The apparatus of claim 1, wherein the over-the-shoulder strap includes a handle extending below the second connector.

7. The apparatus of claim 6, wherein the handle extends downward coupling with a front portion of the torso strap.

8. The apparatus of claim 1, wherein the wrist strap is adapted to extend up over the hand of the wearer leaving a thumb portion open above the carpometacarpal joint.

9. The apparatus of claim 1, wherein the wrist strap is adapted to extend below the elbow of the wearer leaving the elbow exposed above impingements of the Median, Ulnar, or Radial nerves.

10. The apparatus of claim 1, wherein the wrist strap is adapted to extend up the hand and thumb above the interphalangeal joint.

11. The apparatus of claim 1, wherein the wrist strap extends beyond the elbow to substantially halfway up the length of the upper arm of the wearer distributing weight along the entire lower arm.

12. A method for elevating a distal extremity, the method comprising:
    wearing a brace having a wrist strap, and an over the shoulder strap and a torso strap, the wrist strap disposed around a wrist and having a first connector wherein the first connector is a protrusion comprising a first magnet, the over the shoulder strap disposed over a shoulder opposite the distal extremity and having a second connector wherein the second connector is a groove configured to receive the protrusion and comprising a second magnet, and the torso strap disposed around a torso, wherein the groove is open at a top portion such that the wrist strap is disconnected from the over the shoulder strap by moving the wrist strap upwards to slide the first magnet apart from the second magnet, and wherein the groove is closed on a bottom portion and side portions to secure a magnetic connection between the first magnet and the second magnet;
    securing the wrist strap to the over the shoulder strap by aligning and coupling the first connector with the second connector in a coupling direction; and
    adjusting the over the shoulder strap to elevate the wrist strap above a heart.

13. The method of claim 12, further comprising releasing the wrist strap from the over the shoulder strap by applying a force in a direction opposite to coupling direction.

14. The method of claim 12, wherein securing the wrist strap to the over the shoulder strap includes magnetic attraction between the first connector and the second connector.

15. A limb support device for a limb of a wearer, comprising:
- a wrist strap configured to support a portion of an arm of the wearer;
- a first connector on the wrist strap, wherein the first connector is a protrusion comprising a first magnet;
- an over the shoulder strap configured to be worn over a shoulder of the wearer;
- a second connector on the shoulder strap, wherein the second connector is a groove comprising a second magnet, the protrusion receivable within the groove to couple the wrist strap with the over the shoulder strap, wherein the groove is open at a top portion such that the wrist strap is disconnected from the over the shoulder strap by moving the wrist strap upwards to slide the first magnet apart from the second magnet, and wherein the groove is closed on a bottom portion and side portions to secure a magnetic connection between the first magnet and the second magnet;
- wherein when the wrist strap and the shoulder strap are mounted on the wearer, moving the first connector into engagement with the second connecter magnetically couples the first and second connectors to hold the wrist strap in place and transfer the weight of the arm to the wearer's body, and raising the first connector out of engagement with the second connecter decouples the first and second connectors and allows free movement of the arm.

* * * * *